(12) United States Patent
Ueyama (10) Patent No.: US 9,595,152 B2
(45) Date of Patent: Mar. 14, 2017

(54) MAGNETIC PROPERTY DETECTION APPARATUS

(71) Applicant: GLORY LTD., Himeji-shi, Hyogo (JP)

(72) Inventor: Naoki Ueyama, Himeji (JP)

(73) Assignee: GLORY LTD., Himeji-shi, Hyogo (JP)

(*) Notice: Subject to any disclaimer, the term of this patent is extended or adjusted under 35 U.S.C. 154(b) by 0 days.

(21) Appl. No.: 14/778,143

(22) PCT Filed: Mar. 22, 2013

(86) PCT No.: PCT/JP2013/058353
§ 371 (c)(1),
(2) Date: Sep. 18, 2015

(87) PCT Pub. No.: WO2014/147824
PCT Pub. Date: Sep. 25, 2014

(65) Prior Publication Data
US 2016/0071350 A1   Mar. 10, 2016

(51) Int. Cl.
*G01R 33/12* (2006.01)
*G07D 7/04* (2016.01)
(Continued)

(52) U.S. Cl.
CPC .............. *G07D 7/04* (2013.01); *G01N 27/72* (2013.01); *G01R 33/12* (2013.01); *G06K 19/12* (2013.01)

(58) Field of Classification Search
CPC ........... G07D 7/04; G06K 19/12; G01R 33/12
(Continued)

(56) References Cited

U.S. PATENT DOCUMENTS

| 5,451,759 A * | 9/1995 | Hoshino | G06K 7/084 |
| | | | 235/449 |
| 5,552,589 A * | 9/1996 | Smith | G01R 33/09 |
| | | | 235/449 |

(Continued)

FOREIGN PATENT DOCUMENTS

| JP | 4-364498 A | 12/1992 |
| JP | 6-180304 A | 6/1994 |

(Continued)

*Primary Examiner* — Reena Aurora
(74) *Attorney, Agent, or Firm* — Renner, Kenner, Greive, Bobak, Taylor & Weber (57) ABSTRACT

A magnetic property detection apparatus that detects magnetic properties of a magnetic material included in a paper sheet transported through a transport path includes a magnet unit that generates a magnetic field that is perpendicular to a direction of transport of the paper sheet in the transport path and parallel to a transport surface of the paper sheet, of which magnetic field intensity decreases as the paper sheet is being transported in the transport direction, and after the magnetic field intensity has reached 0 (zero), the magnetic field intensity increases with the magnetic field being directed in a reverse direction; and a plurality of magnetic sensors arranged in the magnetic field generated by the magnet unit at locations at which the magnetic field intensity are mutually different, and that detect the magnetic properties of the paper sheet being transported through the transport path. The magnetic properties of the magnetic material included in the paper sheet are detected based on output signals of the plurality of magnetic sensors acquired when the magnetic material is detected.

14 Claims, 7 Drawing Sheets

(51) Int. Cl.
*G01N 27/72* (2006.01)
*G06K 19/12* (2006.01)

(58) Field of Classification Search
USPC .......................................................... 324/228
See application file for complete search history.

(56) References Cited

U.S. PATENT DOCUMENTS

| | | | | |
|---|---|---|---|---|
| 5,644,228 | A * | 7/1997 | Jeffers | G01R 33/09 235/449 |
| 2009/0008922 | A1 * | 1/2009 | Schutzmann | G06K 19/12 283/67 |
| 2010/0327062 | A1 | 12/2010 | Lazzerini | |

FOREIGN PATENT DOCUMENTS

| | | |
|---|---|---|
| JP | 6-180305 A | 6/1994 |
| JP | 3283931 B2 | 5/2002 |
| JP | 2006-293575 A | 10/2006 |
| WO | WO 2009/103352 A1 | 8/2009 |
| WO | WO 2010/052797 A1 | 5/2010 |

* cited by examiner

MAGNETIC PROPERTY DETECTION APPARATUS

TECHNICAL FIELD

The present invention generally relates to a magnetic property detection apparatus that detects magnetic properties of a paper sheet. The present invention more specifically relates to a magnetic property detection apparatus capable of differentiating and detecting a plurality of types of magnetic materials with different magnitudes of coercive force.

BACKGROUND ART

Conventionally, with an object to prevent forgery, magnetic ink including magnetic material has been used to perform printing on paper sheets such as checks, merchandise coupons, etc. The magnetic inks include inks of different magnitudes of coercive force, such as a hard magnetic ink and a soft magnetic ink. If the magnetic inks used to perform printing on a paper sheet can be precisely detected, it can be decided whether the paper sheet is authentic.

An example of a device that detects magnetic ink on paper sheets has been disclosed in Patent Document 1. The magnetic property detection apparatus disclosed in Patent Document 1 generates a magnetic field directed perpendicularly to a transport path of a paper sheet and detects magnetism of the paper sheet when the paper sheet passes through the magnetic field. In this apparatus, an upper unit and a lower unit are arranged above and below the transport path of the paper sheet. Two magnets coupled via a yoke are accommodated in the inside of the upper unit and the lower unit, respectively, and these magnets generate a magnetic field vertically across the transport path. Because the magnetic field is generated at the location of the sensor that detects the magnetism of the paper sheet in a direction perpendicular to the direction of transport of the paper sheet, i.e., in a direction in which the magnetic force is vertically transmitted through the paper sheet, the magnetic ink used to perform printing on the paper sheet can be detected with a high precision.

CITATION LIST

Patent Document

[Patent Document 1] WO 2010/052797 A

SUMMARY OF INVENTION

Technical Problem

However, the above-explained prior art is disadvantageous in that the number of parts increases and therefore the production cost increases because it is necessary to arrange two units that accommodate magnets for generating the magnetic field above and below the transport path. Another problem may arise such that a large-size magnetic property detection apparatus may be necessary to accommodate the two upper and lower units.

Yet another problem may arise, for example, such that if a configuration is employed in which the upper and the lower units are arranged separately from each other, the magnets within these units may be vibrated due to vibration generated during the operation of the transport mechanism and the like, and as a result, noises may be generated therefrom. Further, because the upper and the lower units are arranged above and below the transport path, transport rollers and the like that constitute the transport mechanism cannot be arranged in the transport path located between the upper and the lower units. Accordingly, if the size of the upper and the lower units is large, the paper sheet may not be transported in a stable state.

The present invention has been devised to solve the problems explained above in the prior art. It is an object of the present invention to provide a small-size magnetic property detection apparatus capable of differentiating and detecting a plurality of types of magnetic materials with different magnitudes of coercive force.

Means for Solving Problems

To solve the above problems and to achieve the above objects, according to an aspect of the present invention, a magnetic property detection apparatus that detects magnetic properties of a magnetic material included in a paper sheet transported through a transport path includes a magnet unit that generates a magnetic field that is perpendicular to a direction of transport of the paper sheet in the transport path and parallel to a transport surface of the paper sheet, of which magnetic field intensity decreases as the paper sheet is being transported in the transport direction, and after the magnetic field intensity has reached 0 (zero), the magnetic field intensity increases with the magnetic field being directed in a reverse direction; and a plurality of magnetic sensors arranged in the magnetic field generated by the magnet unit at locations at which the magnetic field intensity are mutually different, and that detect the magnetic properties of the paper sheet being transported through the transport path. The magnetic properties of the magnetic material included in the paper sheet are detected based on output signals of the plurality of magnetic sensors acquired when the magnetic material is detected.

The magnetic property detection apparatus further includes an authenticity determining unit that determines, if a magnetic material included in an authentic paper sheet has been detected and if an output value of a specific magnetic sensor of the plurality of magnetic sensors is 0 (zero), that the paper sheet includes a magnetic material having a specific magnetic property on condition that an output value of any magnetic sensor other than the specific magnetic sensor, of the plurality of magnetic sensors, is other than 0 (zero), and determines that the paper sheet of which magnetism has been detected is an authentic paper sheet.

The magnetic property detection apparatus further includes an authenticity determining unit that determines that if a magnetic material included in an authentic paper sheet has been detected and if no magnetic sensor among the plurality of magnetic sensors exists of which an output value thereof is substantially 0 (zero), the paper sheet to be detected includes a magnetic material having a specific magnetic property when phases of outputs of two specific mutually adjacent magnetic sensors among the plurality of magnetic sensors are opposite to each other, then determines that the paper sheet of which magnetism has been detected is authentic.

The magnetic property detection apparatus further includes a first magnetic sensor that detects magnetic properties of the paper sheet transported through the transport path at a position set based on magnetization characteristics of the magnetic material having a specific coercive force in the magnetic field generated by the magnet unit; and a second magnetic sensor that detects magnetic properties of the paper sheet transported through the transport path at a position different from the position of the first magnetic sensor.

In the magnetic property detection apparatus, wherein the magnet unit at least includes a first magnet that generates a magnetic field in a direction perpendicular to the direction of transport of the paper sheet and parallel to the transport surface of the paper sheet; and a second magnet that generates a magnetic field directed reversely from the direction of the magnetic field generated by the first magnet on a downstream side of the first magnet in the transport direction.

In the magnetic property detection apparatus, the first magnetic sensor is arranged at a position at which the magnetization intensity becomes 0 (zero) after the magnetic material having been magnetized into a saturation magnetization state in the magnetic field is transported in the transport direction based on the magnetization characteristics of the magnetic material having a specific coercive force.

In the magnetic property detection apparatus, if no magnetism has been detected by the first magnetic sensor and if magnetism has been detected by the second magnetic sensor, it is judged that the magnetic material is the magnetic material having a specific coercive force.

In the magnetic property detection apparatus, the coercive force of the detected magnetic material is judged based on phases of a magnetism detection signal output from the first magnetic sensor and a magnetism detection signal output from the second magnetic sensor.

In the magnetic property detection apparatus, the magnetic field generated by the magnet unit has magnetic field intensity for magnetizing the magnetic material to be detected into a saturation magnetization state at a position upstream of the first magnetic sensor in the transport direction.

In the magnetic property detection apparatus, in the magnetic field generated by the magnet unit, the magnetic field intensity gradually decreases to reach 0 (zero), then a series of regions of zero magnetic field continues to be present, and then the magnetic field intensity increases with the magnetic field being directed in a reverse direction.

The magnetic property detection apparatus further includes an adjustment mechanism for changing the magnetic field intensity at a position of arrangement of the first sensor.

The magnetic property detection apparatus according to any one of claims 1 to 11, wherein the first magnetic sensor and the second magnetic sensor are sensors that detect variations of intensity of magnetic flux occurring due to passage of a magnetized magnetic material through a magnetic field.

In the magnetic property detection apparatus, the first magnetic sensor is selected from among the plurality of magnetic sensors arranged at positions at which the magnetic field intensity levels are mutually different based on outputs of the respective magnetic sensors obtained when the magnetic material to be detected is transported through the transport path.

In the magnetic property detection apparatus, when the magnetic material is transported, a magnetic sensor that outputs a positive output and a magnetic sensor arranged adjacent to the magnetic sensor and that outputs a negative output are selected among the plurality of magnetic sensors and the two magnetic sensors are used as the first magnetic sensor.

Advantageous Effects of Invention

According to the present invention, the magnet unit is arranged either above or below the transport path for transporting the magnetic material to be subjected to magnetic detection and the magnetic field is generated in a direction perpendicular to the magnetic material transport direction and in a direction parallel to the transport side to detect the magnetism. Accordingly, the size and the production costs of the magnetic property detection apparatus can be reduced.

Moreover, a plurality of magnetic sensors are arranged at locations of different magnetic field intensity and a magnetic sensor to be used can be selected, and the magnetic sensor is selected according to the magnetic material included in the paper sheet to be processed. Accordingly, the magnetic properties included in various paper sheets can be detected, and the authenticity of the paper sheet can be determined.

Furthermore, the magnetic field for detecting the magnetic material can be generated by using only two magnets. Accordingly, the size and the production costs of the magnetic property detection apparatus can be reduced.

Moreover, two magnetic sensors are used, the first magnetic sensor is arranged at a location at which the output value at the time a predetermined magnetic material passes becomes substantially 0 (zero) according to the magnetization characteristics of the magnetic material, and the second magnetic sensor is arranged at a location at which the output according to the magnetized state can be obtained when the magnetic material passes. Accordingly, the passage of the magnetic material can be detected with a high precision.

Furthermore, when a magnetic material is detected, whether the magnitude of the coercive force of the detected magnetic material is higher (or lower) than the magnitude of the coercive force of the magnetic material used in setting the location of arrangement of the first magnetic sensor can be determined based on which of the same phase and the mutually opposite phases the output signals of the first magnetic sensor and the second magnetic sensor output when the magnetic material is detected are. Accordingly, a plurality of types of magnetic materials can be detected and differentiated.

Moreover, the magnetic field intensity at the location of arrangement of the first sensor can be changed. Accordingly, the magnetic properties of various magnetic materials can be precisely detected by changing the magnetic field intensity according to the magnetic material to be detected.

BRIEF DESCRIPTION OF DRAWINGS

FIGS. 6A, 63 and 6C are views that illustrate examples in which the locations of arrangement or the magnitudes of magnetic force of the two magnets used in the magnetic property detection apparatus are different.

DESCRIPTION OF EMBODIMENTS

Exemplary embodiments of the magnetic property detection apparatus according to the present invention will be explained in detail below with reference to accompanying drawings. The magnetic property detection apparatus according to the present embodiment includes a function for detecting magnetism of magnetic material such as magnetic ink and the like used to perform printing on paper sheets such as checks, merchandise coupons, and valuable securities. The magnetic property detection apparatus is used in a paper sheet handling apparatus, for example, to determine whether a paper sheet is an authentic paper sheet or not by detecting magnetic properties of the magnetic material contained in the paper sheet. The magnetic material that is the object of detection by the magnetic property detection apparatus is not particularly limited, and an example will be explained below in which a magnetic ink used to perform printing on paper sheets is taken as the object of detection.

Figure 1A:
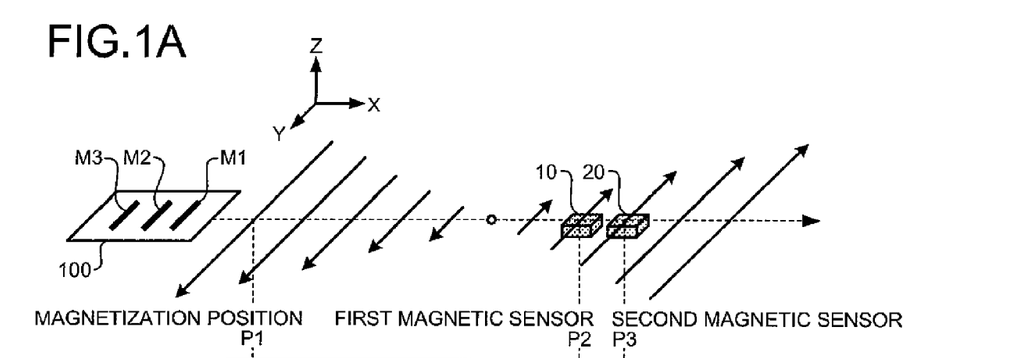
FIGS. 1A, 1B and 1C are schematic charts for explaining a magnetic property detection method performed by a magnetic property detection apparatus according to an embodiment of the present invention.
Figure 1B:
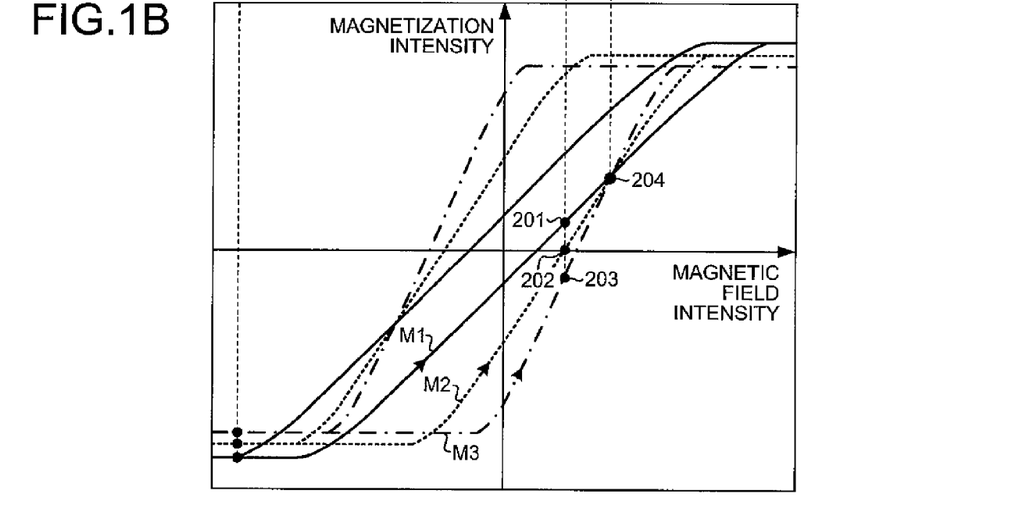
Figure 1C:
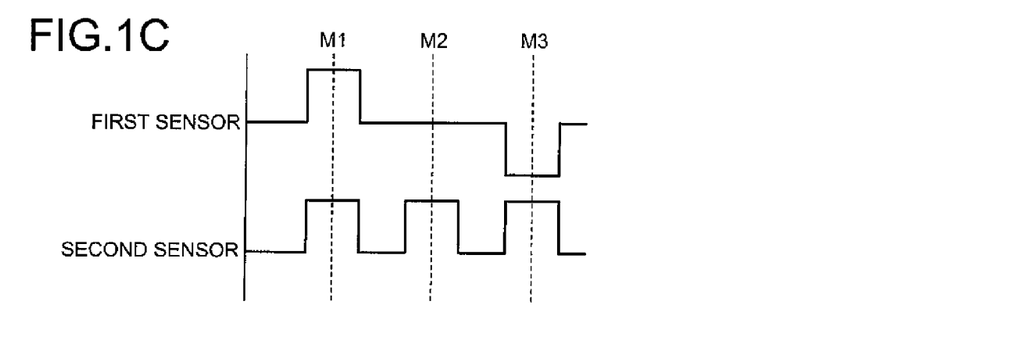

FIG. 1A to FIG. 1C are schematic view that illustrates a magnetic property detection method of detecting a magnetic material by using the magnetic property detection apparatus. FIG. 1B illustrates saturation magnetization curves for a plurality of types of magnetic inks M1 to M3, which are the objects of the detection, and FIG. 1A illustrates an outline configuration of the magnetic property detection apparatus that differentiates and detects the magnetic inks M1 to M3. FIG. 1C illustrates output signals from sensors acquired when the magnetic inks M1 to M3 shown in FIG. 1B are detected by the magnetic property detection apparatus having the configuration shown in FIG. 1A. The magnitudes of the coercive force of the magnetic inks M1 to M3 satisfy a relationship M3>M2>M1. Output signals from the magnetic sensors explained below in the present embodiment represent variations of values of resistance of magneto-resistive elements as voltage values, for example.

The magnetic property detection apparatus includes a magnet unit that generates a magnetic field and a first magnetic sensor 10 and a second magnetic sensor 20 that detect a magnetic material passing through the magnetic field. The first magnetic sensor 10 and the second magnetic sensor 20 are sensors that use a magnetic detection element for detecting changes in the density of the magnetic flux of a bias magnetic field, which occur due to the passage of the magnetic material. For the magnetic sensors, other than magneto-resistive elements such as an anisotropic magneto-resistive element (AMR element), a semiconductor magneto-resistive element (SMR element), and a giant magneto-resistive element (GMR element) can be used, a Hall Effect sensor and the like can be used. The first magnetic sensor 10 and the second magnetic sensor 20 include a magnetic detection element arranged so as to detect fluctuation of the magnetic field in the vertical direction (i.e., in the Z-axis direction) or in the transporting direction (i.e., in the X-axis direction) occurring in relation to the surface of a transported paper sheet 100. In FIG. 1A, the magnetic field generated by the magnet unit only is shown, and details of the magnet unit will be explained below.

In FIG. 1A, a broken line arrow indicates a direction of transport of the paper sheet 100 through the transport path, and the direction and the length of solid lines indicate the direction of the magnetic field and the magnetic field intensity, respectively. In the magnetic property detection apparatus explained in Patent Document 1, the magnetic field is generated in a direction perpendicular (i.e., in the Z-axis direction) to the direction of transport of the paper sheet 100 (i.e., the X-axis direction) and the transport surface (i.e., the X-Y plane). On the contrary, as shown in FIG. 1A, in the magnetic property detection apparatus according to the present embodiment, it is one of the characteristics of the apparatus to generate the magnetic field in a direction perpendicular to the direction of transport of the paper sheet 100 (i.e., the X-axis) and parallel to the transport surface of the paper sheet 100 (i.e., the X-Y plane).

With regard to the magnetic field of the magnetic property detection apparatus, the magnetic field intensity gradually decreases from a location on the upstream of the first magnetic sensor 10 in the transport direction at which the magnetic material to be detected is magnetized to reach 0 (zero), and then the magnetic field intensity gradually increases with a reversely oriented magnetic field. If the magnetic inks M1 to M3 are to be detected, the magnetic field intensity at the magnetizing position P1, where the magnetic inks M1 to M3 are magnetized, is set so that the state of the magnetic inks M1 to M3 become a saturation magnetization state at the magnetizing position P1. It is preferable that the value of the magnetizing force at the magnetizing position P1 is set twice as large as the maximum coercive force of the magnetic material to be magnetized or more but the magnetic field intensity at the magnetizing position P1 is three times as large as the maximum coercive force of the magnetic material or more, for example.

When the coercive forces of the magnetic inks M1 to M3 are larger in order of M1, M2, M3 as shown in FIG. 1B, the first magnetic sensor 10 is arranged at a position P2 on the transport path corresponding to a point 202 at which the intensity of magnetization of the magnetic ink M2 having been turned into the saturation magnetization state at the magnetizing position P1 becomes 0 (zero) on the saturation magnetization curve. In other words, the first magnetic sensor 10 is arranged at the position P2 corresponding to the magnetic field intensity at which the intensity of magnetization of the magnetic ink M2 having been magnetized into the saturation magnetization state and transported through the transport path becomes 0 (zero).

The location of arrangement of the second magnetic sensor 20 is not particularly limited and can be arranged at any location other than the position P2. For example, the second magnetic sensor 20 can be arranged at a position P3 on the transport path and corresponding to a point 204 at which the saturation magnetization curves for the magnetic inks M1 to M3 cross one another. In other words, the second magnetic sensor 20 is arranged at the position P3 corresponding to the magnetic field intensity at the point 204 on the saturation magnetization curves shown in FIG. 1B.

Referring to FIG. 1A, when the paper sheet 100 including the magnetic inks M1 to M3 is transported through the magnetic field along the transport path, first, all the magnetic inks M1 to M3 are magnetized into the saturation magnetization state at the magnetizing position P1.

When the paper sheet 100 is transported along the transport path and the magnetic ink M1 reaches the position P2 first, the first magnetic sensor 10 detects the magnetization intensity corresponding to a point 201 on the saturation magnetization curve for the magnetic ink M1 shown in FIG. 1B. Next, when the magnetic ink M2 reaches the position P2, the result of the detection by the first magnetic sensor 10 is 0 (zero) corresponding to the point 202 on the saturation magnetization curve for the magnetic ink M2. When the magnetic ink M3 reaches the position P2, the first magnetic sensor 10 detects the magnetization intensity corresponding to the point 203 on the saturation magnetization curve for the magnetic ink M3. At the position P2, the magnetization intensity for the magnetic ink M1 (the point 201) is in the upper right quadrant and the magnetization intensity for the magnetic ink M3 (the point 203) is in the lower left quadrant, and as can be understood from this, the results of detection by the first magnetic sensor 10 are in the mutually opposite phases for the magnetic ink M1 and the magnetic ink M3.

When the paper sheet 100 is further transported and reaches the position P3, the results of detection by the second magnetic sensor 20 for the magnetic inks M1 to M3 are the same because the magnetic ink M1 has the magnetization intensity corresponding to the point 204 on the saturation magnetization curve shown in FIG. 1B. In other words, results of the detection in the same phase are acquired as a result of the detection by the second magnetic sensor 20 for all the magnetic inks M1 to M3.

As a result, as shown in FIG. 1C, the first magnetic sensor 10 outputs signals of mutually opposite phases at the timing of passage of the magnetic ink M1 and at the timing of passage of the magnetic ink M3, and the output signal at the timing of passage of the magnetic ink M2 is substantially 0 (zero). The second magnetic sensor 20 outputs signals in the same phase for the magnetic inks M1 to M3 having substantially same magnitude.

In FIG. 1C, corresponding sensor outputs are vertically arranged to facilitate comparison of the results of detection for the magnetic inks M1 to M3 by the first magnetic sensor 10 and the second magnetic sensor 20; however, during actual measurements, the timing of measurement by the first magnetic sensor 10 and the timing of measurement by the second magnetic sensor 20 has a time difference that depends on the transport distance from the position 22 to the position P3 and the transport speed therefor. The magnetic property detection apparatus, by operating in cooperation with a not-shown transport mechanism for transporting the paper sheet 100, recognizes a relationship between the location of the paper sheet 100 and the output values from the first magnetic sensor 10 and the second magnetic sensor 20. Accordingly, as shown in FIG. 1C, the correspondence between the results of the detection for the respective magnetic inks M1 to M3 acquired by the first magnetic sensor 10 and the results of the detection for the respective magnetic inks M1 to M3 acquired by the second magnetic sensor 20 can be recognized. However, the present embodiment is not limited to the configuration in which the correspondence between the location of the paper sheet 100 and the results of detection of the magnetism is identified by the magnetic property detection apparatus. For example, it is also possible to employ a configuration in which another apparatus connected to both the transport mechanism and the magnetic property detection apparatus identifies such a correspondence based on location information acquired from the transport mechanism and detection information about the magnetism acquired from the magnetic property detection apparatus.

Whether the detected magnetic material is the magnetic ink M1, M2, or M3 can be determined by comparing the sensor outputs from the first magnetic sensor 10 and those from the second magnetic sensor 20 acquired in the above-explained manner. Specifically, if the sensor outputs in the same phase have been acquired from the first magnetic sensor 10 and the second magnetic sensor 20, it is determined that the detected magnetic material is the magnetic ink M1, and if the sensor outputs in the opposite phases have been acquired from the first magnetic sensor 10 and the second magnetic sensor 20, it is determined that the detected magnetic material is the magnetic ink M3.

If magnetism has been detected by the second magnetic sensor 20 even when the value of the sensor output from the first magnetic sensor 10 is substantially 0 (zero), it is determined that the detected magnetic material is the magnetic ink M2. If the output value of the first magnetic sensor 10 is substantially 0 (zero), it cannot be determined which of the detection result indicating that the magnetic material is the magnetic ink M2 and the detection result indicating absence of a magnetic material the detection result is based on the output from the first magnetic sensor 10 only; however, it can be determined that the detected magnetic material is the magnetic ink M2 based on the magnetism detected by the second magnetic sensor 20.

Accordingly, because the magnetic property detection apparatus according to the present embodiment is capable of detecting and differentiating the magnetic inks with different magnitudes of coercive force, if magnetic inks with different magnitudes of coercive force is used on an authentic paper sheet 100, it can be determined that the paper sheet 100 is authentic by detecting the respective magnetic inks.

In the example shown in FIG. 1, the paper sheet 100 includes three magnetic inks M1 to M3 to explain that the present embodiment is capable of differentiating and recognizing a plurality of magnetic inks with different magnitudes of coercive force; however, if only one magnetic ink M2 is included in an authentic paper sheet 100, for example, if the magnetic ink M2 is detected, it can be determined that the paper sheet 100 is authentic, and on the contrary, if no magnetism is detected or if different magnetic inks such as the magnetic inks M1 and M3 are detected, it can be determined that the paper sheet 100 is not authentic.

Figure 2A:
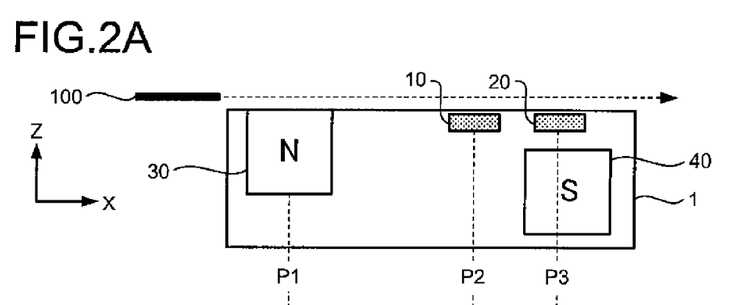
FIGS. 2A, 2B and 2C are views that schematically illustrate a configuration of the magnetic property detection apparatus according to the present embodiment.
Figure 2B:
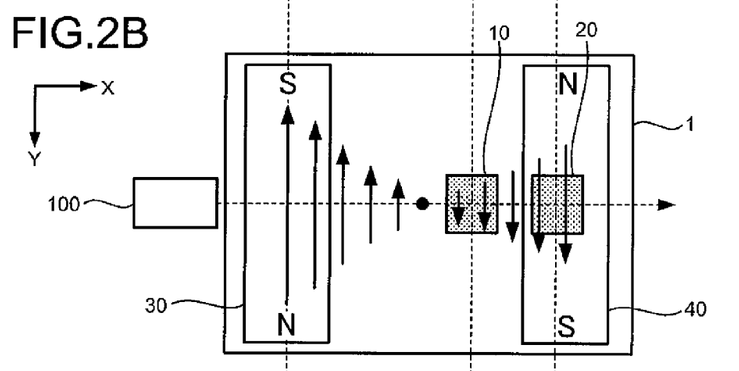
Figure 2C:
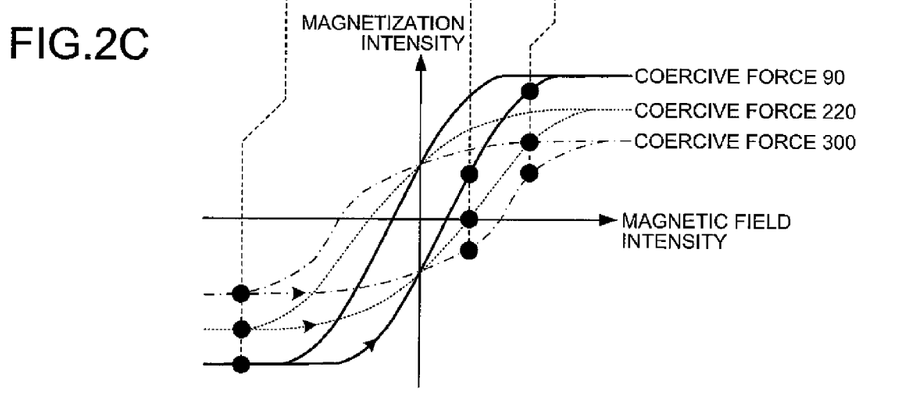

Next, a configuration of the magnetic property detection apparatus will be explained. FIG. 2A to FIG. 2C are views that illustrate an outline configuration of a magnetic property detection apparatus 1. FIG. 2A shows the configuration of the magnetic property detection apparatus 1 viewed from the Y-axis direction, and FIG. 2B shows the configuration viewed from the Z-axis direction. FIG. 2C is a view that illustrates a relationship between the locations of arrangement of the first magnetic sensor 10 and the second magnetic sensor 20 used in the magnetic property detection apparatus 1 and the coercive forces of the magnetic inks to be detected.

In the following drawings including FIG. 2A to FIG. 2C, a broken line arrow indicates the direction of transport of the paper sheet 100, and the direction and the length of solid lines indicate the direction of the magnetic field and the magnetic field intensity, respectively.

Referring to FIG. 2A, the magnetic property detection apparatus 1 is installed and used below the transport path through which the paper sheet 100 is to be transported. The magnetic property detection apparatus 1 includes two magnets 30 and 40 that form a magnet unit that generates the magnetic field; and the first magnetic sensor 10 and the second magnetic sensor 20 that detect the variation of the density of the magnetic flux generated according to the magnetic properties of the paper sheet 100 that passes through the bias magnetic field.

The paper sheet 100 is transported, by a not-shown transport mechanism constituted by rollers and the like, on the magnetic property detection apparatus 1 toward the X-axis direction. A signal related to the timing of transport by the transport mechanism is inputted to the magnetic property detection apparatus 1. Upon receipt of this signal, output signals from the sensors are recorded while identifying the location of the paper sheet 100 passing through the respective locations of the first magnetic sensor 10 and the second magnetic sensor 20. The magnetic property detection apparatus 1 includes a not-shown processing circuit board that processes signals output from the first magnetic sensor 10 and the second magnetic sensor 20. For the transport mechanism that transports the paper sheet 100, the measurement method that uses the information about the location of the paper sheet 100 transported by the transport mechanism, and the measurement circuit and the measurement method that use various types of magnetic detection elements such as a magneto-resistive element (MR element) and Hall effect sensors, detailed descriptions thereof will be omitted because known technology can be used therefor, and characteristics of the configuration of the magnetic property detection apparatus 1 will be explained below.

The two magnets 30 and 40, with a shape of a rectangular solid, that form the magnet unit are arranged so that their long edge sides are parallel to the Y-axis direction and that they are to be distant from each other in the X-axis direction with the respective polarity being opposite to each other. With this configuration, as shown in FIG. 2B by the solid line arrows, the magnetic field is oriented in a direction parallel to the transport surface of the paper sheet 100 (the X-Y plane) and perpendicular to the direction of transport of the paper sheet 100 (X-axis direction) (i.e., in a direction toward the negative side on the Y-axis) at a position of the magnet 30 located on the upstream side of the first magnetic sensor 10 in the transport direction, and the magnetic field is oriented in an opposite direction (toward the positive side on the Y-axis) at a position of the magnet 40 located on the downstream side of the first magnetic sensor 10 in the transport direction. Because the two magnets 30 and 40 are arranged with their polarity being opposite to each other, the magnetic field intensity gradually decreases as one goes away from the magnetizing position P1 in the transport direction, and after the magnetic field intensity has reached 0 (zero) at a position between the two magnets 30 and 40, the magnetic field intensity gradually increases with the magnetic field being reversely oriented.

The magnetic ink on the paper sheet 100 to be detected is magnetized into a saturation magnetization state at the magnetizing position P1 located on the downstream side of the first magnetic sensor 10 and the second magnetic sensor 20 in the transport direction. Referring to FIG. 2C, for example, if three types of magnetic inks having coercive forces of 90 Oe, 220 Oe, and 300 Oe are to be detected, the magnetic field intensity at the magnetizing position P1 is set so as to be twice or more than the maximum coercive force of 300 Oe, and the magnetic field intensity at the magnetizing position P1 is set at 900 G, for example, which is three times as high as the maximum coercive force.

The locations of arrangement of the first magnetic sensor 10 and the second magnetic sensor 20 are set based on the magnetic field generated by the magnets 30 and 40 and the magnetization characteristics of the magnetic ink to be detected. For example, among the three types of magnetic inks with the coercive force of 90 Oe, 220 Oe, and 300 Oe shown in FIG. 2C, based on the magnetization characteristics of the magnetic ink with the medium-value coercive force of 220 Oe, the first magnetic sensor 10 is arranged at the position P2, at which the magnetic field intensity becomes 0 (zero) after the above magnetic ink has traveled through the magnetic field along the transport path and turned into the saturation magnetization state at the magnetization position P1. The second magnetic sensor 20 is arranged at a position different from the position P2 at which the first magnetic sensor 10 is arranged. For example, a second magnet (the second magnetic sensor) 20 is arranged at the position P3 with the same coordinate positions as those of the first magnetic sensor 10 in the direction of the transport path (Y-axis direction) and in the height direction (Z-axis direction), which is a position distant from the first magnetic sensor toward the downstream side in the transport direction (X-axis direction). To arrange the second magnetic sensor 20 below the transport path and above the magnet 40, the location of arrangement of the magnet 40 in the height direction (Z-axis direction) is lower than the location of arrangement of the magnet 30 on the upstream side.

Referring to FIGS. 2A and 2B, if the location of arrangement of the first magnetic sensor 10 is set to the position P2 and the location of arrangement of the second magnetic sensor 20 is set to the position P3 based on the magnetization characteristics of the magnetic ink with the coercive force of 220 Oe and the magnetic field intensity of the bias magnetic field, then as can be understood from the saturation magnetization curve shown in FIG. 2C, the output value of the first magnetic sensor 10 is substantially 0 (zero) when the magnetic ink with the coercive force of 220 Oe has been detected, while the sensor output according to the magnetization intensity is obtained from the second magnetic sensor 20. For the magnetic ink with the coercive force of 90 Oe, which is lower than 220 Oe, both the magnetization intensity corresponding to the position P2 and the magnetization intensity corresponding to the position P3 are in the upper right quadrant, and thus signals in the same phase are output from the first magnetic sensor 10 and the second magnetic sensor 20. On the contrary, for the magnetic ink with the coercive force of 300 Oe, which is higher than 220 Oe, the magnetization intensity corresponding to the position P2 is in the lower left quadrant while the magnetization intensity corresponding to the position P3 is in the upper right quadrant, and thus signals in mutually opposite phases are detected from the first magnetic sensor 10 and the second magnetic sensor 20.

Figure 3A:
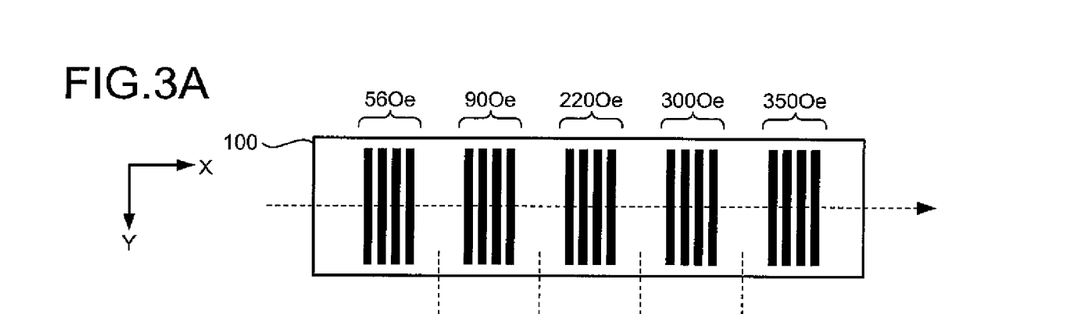
FIGS. 3A, 3B and 3C are views that illustrate examples of detection signals acquired by the magnetic property detection apparatus when magnetic patterns are printed on a paper sheet using a plurality of types of magnetic inks with different magnitudes of coercive force.
Figure 3B:
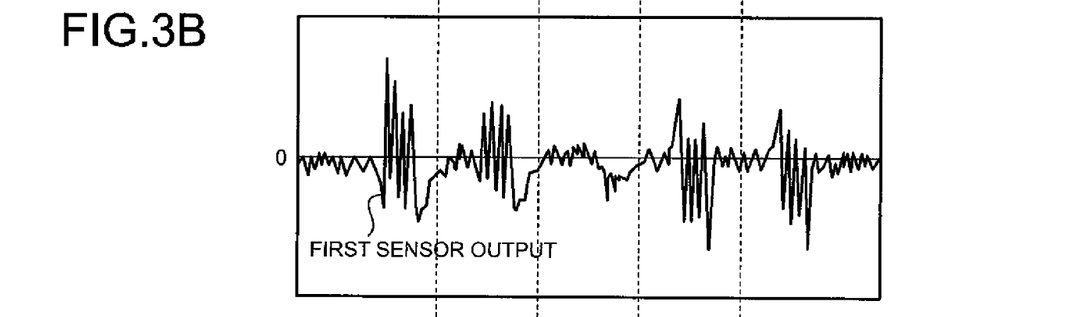
Figure 3C:
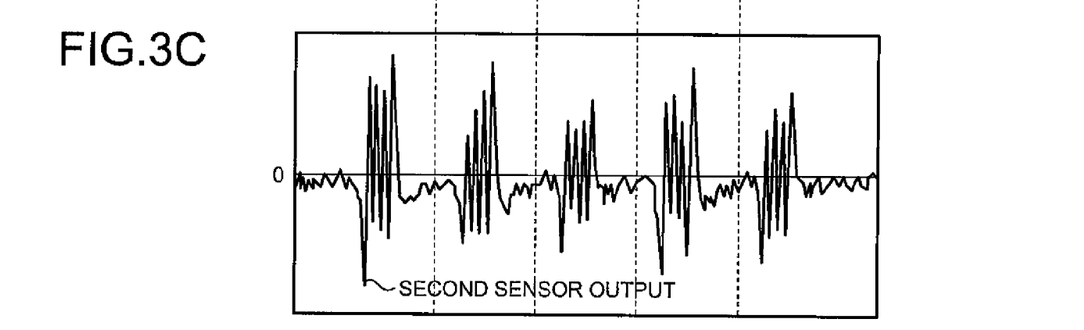

Next, concrete example of the detection signal acquired when the magnetic material is detected by the magnetic property detection apparatus 1 shown in FIG. 2 will be explained. FIG. 3A to FIG. 3C are views that illustrate examples of detection signals acquired by the magnetic property detection apparatus 1 when magnetic patterns are printed on the paper sheet 100 by using five types of magnetic inks with different magnitudes of coercive force. Referring to FIG. 3A, magnetic patterns respectively formed by four straight lines are formed on the paper sheet 100 by using magnetic inks with the coercive force of 56 Oe, 90 Oe, 220 Oe, 300 Oe, and 350 Oe. By performing detection of the magnetism of the magnetic material included in the paper sheet 100 by using the magnetic property detection apparatus 1 shown in FIG. 2A, a detection signal shown in FIG. 3B is obtained from the first magnetic sensor 10 while a detection signal shown in FIG. 3C is obtained from the second magnetic sensor 20. The magnetic patterns shown in FIG. 3A and the detection signals from the respective sensors obtained in relation to the respective magnetic patterns are aligned and shown so as to be vertically arranged in FIG. 3A and FIG. 3B.

Because the first magnetic sensor 10 is arranged at the position P2 at which the magnetization intensity of the magnetic ink with the coercive force of 220 Oe becomes 0 (zero), as shown in FIG. 3B, the detection signal from the first magnetic sensor 10 when the magnetic ink with the coercive force of 220 Oe passes the position P2 is substantially 0 (zero). For the detection signals obtained by detection by the first magnetic sensor 10 for the magnetic ink with the coercive force of 56 Oe and the magnetic ink with the coercive force of 90 Oe, which are lower than 220, i.e., the magnetic inks of which the magnetization intensity is in the upper right quadrant in FIG. 2C, four peaks are formed, which correspond to four magnetic patterns on the positive side, formed as the value falls from substantially 0 (zero) into the negative side once and then rises to the positive side, as shown in FIG. 3B. For the detection signals obtained by detection by the first magnetic sensor 10 for the magnetic ink with the coercive force of 300 Oe and the magnetic ink with the coercive force of 350 Oe, which are higher than 220, i.e., the magnetic inks of which the magnetization intensity is in the lower left quadrant in FIG. 2C, four peaks are formed, which correspond to four magnetic patterns on the negative side, formed as the value rises from substantially 0 (zero) into the positive side once and then falls to the negative side, as shown in FIG. 3B.

For the second magnetic sensor 20, because the magnetization intensity of the magnetic ink with the coercive force of 220 Oe is in the upper right quadrant as shown in FIG. 2C, four peaks are formed, which correspond to four magnetic patterns on the positive side, formed as the value falls from substantially 0 (zero) into the negative side once and then rises to the positive side, as shown in FIG. 3C. For the magnetic ink with the coercive force of 56 Oe and the magnetic ink with the coercive force of 90 Oe, the magnetization intensity on the saturation magnetization curve is in the upper right quadrant at the position P3, and thus the waveform of the detection signal from the second magnetic sensor 20 is in the same phase as that of the detection signal from the first magnetic sensor 10, and accordingly, four peaks are formed on the positive side, which are formed as the value falls from substantially 0 (zero) into the negative side once and then rises to the positive side. For the magnetic ink with the coercive force of 300 Oe and the magnetic ink with the coercive force of 350 Oe, the magnetization intensity on the saturation magnetization curve is in the upper right quadrant at the position P3, and thus the waveform of the detection signal from the second magnetic sensor 20 is in the phase opposite to that of the detection signal from the first magnetic sensor 10, and accordingly, four peaks are formed on the positive side, which are formed as the value falls from substantially 0 (zero) into the negative side once and then rises to the positive side.

As explained above, if the output value from the first magnetic sensor 10 is substantially 0 (zero) and if a detection signal corresponding to the magnetic ink with the coercive force of 220 Oe has been acquired from the second magnetic sensor 20, then the magnetic property detection apparatus 1 shown in FIG. 2B can determine that the detected magnetic material is the magnetic ink with the coercive force of 220 Oe. If the output signals from the first magnetic sensor 10 and the second magnetic sensor 20 are in the same phase, it is determined that the magnetic material is a magnetic ink with the coercive force lower than 220 Oe, and on the contrary, if the output signals from the first magnetic sensor 10 and the second magnetic sensor 20 are in the mutually opposite phases, then it is determined that the magnetic material is a magnetic ink with the coercive force higher than 220 Oe.

In the present embodiment, as explained above, in the magnetic property detection apparatus 1 shown in FIG. 2B, the first magnetic sensor 10 is arranged at the position P2 at which the magnetization intensity is 0 (zero) based on the magnetization characteristics of a predetermined magnetic ink; however, the present embodiment is not limited to the configuration in which the magnetic field intensity at the location of arrangement of the first magnetic sensor 10 is fixed to a predetermined value. In an alternative configuration, the magnetic field intensity can be set variable. For example, if the magnitudes of coercive force of the magnetic inks used on an authentic paper sheet 100 differ according to the types of the paper sheet 100, and if the magnetic field intensity at the location of arrangement of the first magnetic sensor 10 can be changed according to the type of the paper sheet 100, then determination on the authenticity of respective paper sheet 100 can be precisely performed.

Figure 4A:
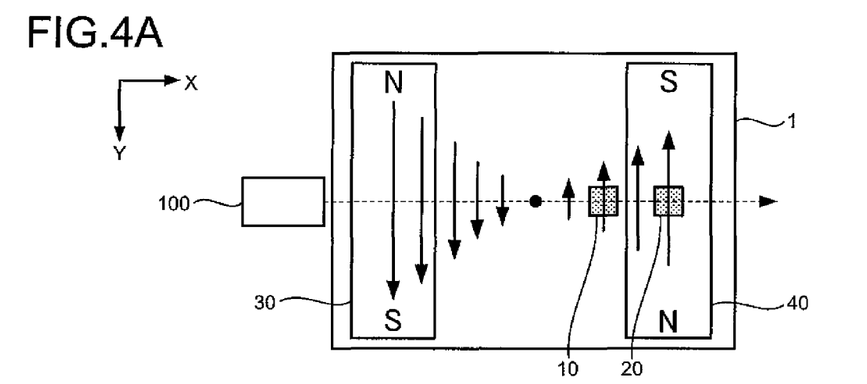
FIGS. 4A, 4B, 4C and 4D are views that illustrate a method of adjusting and changing, which is performed by the magnetic property detection apparatus, the magnetic field intensity at the location of arrangement of the first magnetic sensor.
Figure 4B:
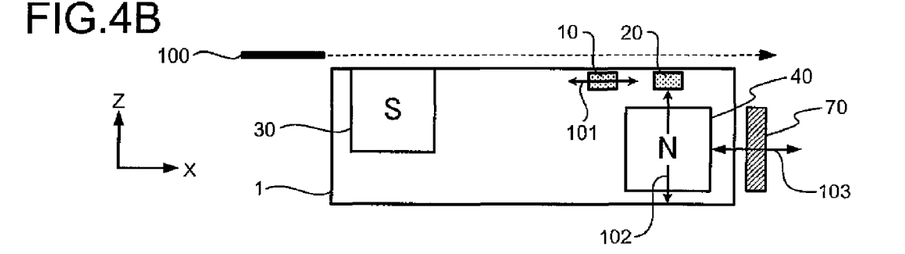

FIG. 4A to FIG. 4D are views that illustrate a method of adjusting and changing the magnetic field intensity at the location of arrangement of the first magnetic sensor 10 by using the magnetic property detection apparatus 1. If the first magnetic sensor 10 is arranged so that the location thereof can be adjusted in a direction indicated by an arrow 101 as shown in FIG. 4B, then the magnetic field intensity at the location of arrangement of the first magnetic sensor 10 can be changed. Similarly, if the position of the magnet 40 can be adjusted in the direction indicated by an arrow 102, then the magnetic field intensity at the location of arrangement of the first magnetic sensor can be changed. Alternatively, if a yoke 70 is arranged to the side of the magnet 40 and if the location of the yoke 70 is adjustable in the direction indicated by an arrow 103, similarly, the coercive force at the location of arrangement of the first magnetic sensor 10 can be changed. For an adjustment mechanism for adjusting and changing the locations of the first magnetic sensor 10, the magnet 40, and the yoke 70, known technology such as a stage with a position adjustment mechanism and the like used in the fields of precision apparatuses and optical apparatuses, for example, can be used, and accordingly, detailed descriptions thereof will be omitted here.

Figure 4C:
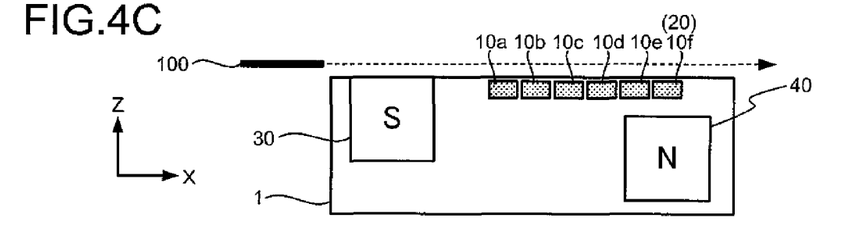

In an alternative configuration, the magnetic field intensity at the location of arrangement of the first magnetic sensor 10 may be changed by a method in which a plurality of magnetic sensors 10*a* to 10*f* are arranged, as illustrated in FIG. 4C, at locations of different magnetic field intensity and the sensor to be used for measurement is selected.

For example, while using the second magnetic sensor 10*f* arranged above the magnet 40 similarly to FIG. 4B as the second magnetic sensor 20, the sensor to be used as the first magnetic sensor 10 can be selected from among the plurality of magnetic sensors 10*a* to 10*e*. In an alternative configuration, the first magnetic sensor 10 and the second magnetic sensor 20 can be selected and used from among all the magnetic sensors 10*a* to 10*f*. For example, the sensors to be used as the first magnetic sensor 10 and the second magnetic sensor 20 are previously selected from among the plurality of magnetic sensors 10*a* to 10*f* and set as the first magnetic sensor 10 and the second magnetic sensor 20 according to the magnetic material included in the paper sheet 100 to be detected. The detection of the magnetic properties is performed by selecting and switching the first magnetic sensor 10 and the second magnetic sensor 20 used for the measurement according to the type of the paper sheet 100 based on the setting.

Figure 4D:
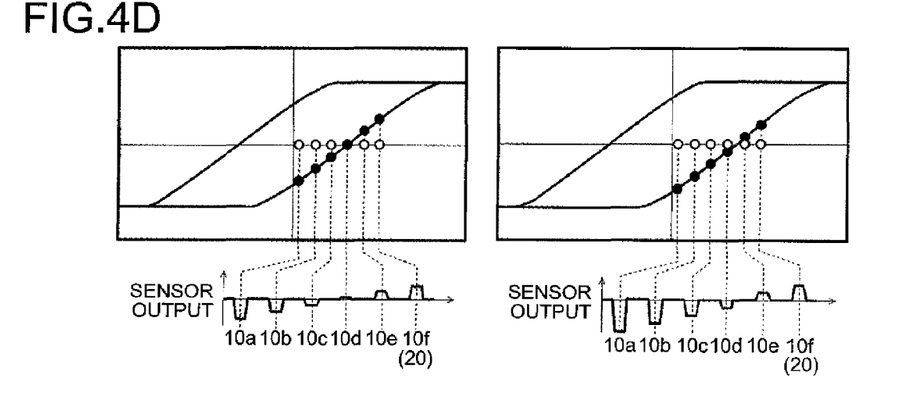

In yet another alternative configuration, the sensor to be used can be selected according to results of measurement obtained by performing the measurement by using all the magnetic sensors 10a to 10f. FIG. 4D are views that illustrate relationships between the saturation magnetization curve for the magnetic material to be detected and the sensor output from the magnetic sensors 10a to 10f. The left view of FIG. 4D shows an example in which a magnetic sensor of which the output value is substantially 0 (zero) when the magnetic material has been detected exists, and the right view of FIG. 4D shows an example in which no magnetic sensor of which the output value is substantially 0 (zero) when the magnetic material has been detected exists. Although not illustrated in the upper saturation magnetization curve of FIG. 4D, the magnetization intensity is taken on the ordinate axis while the magnetic field intensity is taken on the abscissa axis, similar to FIG. 1B and FIG. 2C.

For example, the magnetic material to be detected is transported as shown in FIG. 4C, and if the sensor outputs shown in the left portion of FIG. 4D has been obtained from the magnetic sensors 10a to 10f, the magnetic sensor 10d of which the output value is substantially 0 (zero) is selected. In processing the paper sheet 100 including the magnetic material, the selected magnetic sensor 10d is used as the first magnetic sensor 10. The second magnetic sensor 20 can be arranged at a location other than the location of arrangement of the first magnetic sensor 10, and similarly to FIG. 4B, the magnetic sensor 10f is used as the second magnetic sensor 20, for example.

Depending on the coercive force of the magnetic material, no magnetic sensor of which the output value is substantially 0 (zero) exists among the magnetic sensors 10a to 10f, and as illustrated in the right view of FIG. 4D, sensor outputs of opposite signs can be obtained from the mutually adjacent magnetic sensors 10d and 10e in some cases. In this case, two magnetic sensors 10d and 10e are selected and used as the first magnetic sensor 10. Specifically, if a positive output is obtained from one magnetic sensor 10d and a negative output is obtained from the other magnetic sensor 10e, then a process is performed assuming that the magnetic material of which the output value is substantially 0 (zero) at a position in between them has been detected by the first magnetic sensor 10. In this case also, the sensor to be used as the second magnetic sensor 20 can be a sensor other than the magnetic sensors 10d and 10e used as the first magnetic sensor 10, and the magnetic sensor 10f can be used as the second magnetic sensor 20. With the above-explained configuration, the functions and the operations of the magnetic property detection apparatus 1 explained above can be implemented.

If the sensor outputs shown in the right view of FIG. 4D have been obtained, the magnetic sensor 10d or 10e, of which the output value is close to 0 (zero), can be selected and used as the first magnetic sensor 10. In an alternative configuration, based on the sensor output values shown in the right view of FIG. 4D, supposing that a virtual sensor of which the output value is 0 (zero) exists between the mutually adjacent magnetic sensors 10d and 10e, the virtual sensor can be used as the first magnetic sensor 10 for the process.

By selecting the first magnetic sensor 10 based on the results of measurement of the magnetic material or by setting a virtual sensor based on the output value of the two mutually adjacent sensors and using the set virtual sensor, even if a magnetic material having a new magnetic property is added to detection object magnetic materials, the location of the first magnetic sensor 10 can be set according to the newly added magnetic material.

As indicated by the saturation magnetization curves shown in FIG. 4D, by using the phases of a plurality of sensor outputs, authenticity of the paper sheet 100 can be determined based on the magnetic properties of the magnetic material included in the paper sheet 100. For example, if the phases of the output signals of predetermined mutually adjacent magnetic sensors are opposite to each other, it can be determined that the paper sheet 100 is authentic because the paper sheet 100 includes the magnetic material with authentic magnetic properties. For example, if the upper portions of FIG. 4D indicate the magnetization characteristics of an authentic paper sheet 100 and if the sensor outputs shown in the lower portions of FIG. 4D have been obtained, then it can be determined that the paper sheet 100 is authentic based on the coercive force of the paper sheet 100 calculated from the output signals of the magnetic sensors 10d and 10e.

In an alternative configuration, the magnetic properties of the magnetic material can be determined based on the sensor outputs of the plurality of magnetic sensors 10a to 10f shown in FIG. 4. In this configuration, the output values from the respective magnetic sensors obtained at the timing of passage of the magnetic material above the plurality of magnetic sensors 10a to 10f are compared with one another, and if any magnetic sensor exists of which the output value is substantially 0 (zero), it can be determined that the coercive force of the magnetic material to be detected is close to the magnetic field intensity corresponding to the magnetic sensor of which the output value is substantially 0 (zero). On the contrary, if no magnetic sensor exists of which the output value is substantially 0 (zero) and if the signs of the output values of the mutually adjacent magnetic sensors are opposite to each other, it can be determined that the coercive force of the magnetic material is between the magnetic field intensity corresponding to the magnetic sensor that has outputted a positive output and the magnetic field intensity corresponding to the magnetic sensor that has outputted a negative output value. If the output values of all the magnetic sensors are negative, it can be determined that the coercive force of the detection object magnetic material is equal to or higher than the magnetic field intensity corresponding to the magnetic sensor 10f, and if the output values of all the magnetic sensors are positive, it can be determined that the coercive force of the magnetic material is 0 (zero) or higher and equal to or lower than the magnetic field intensity corresponding to the magnetic sensor 10a. For example, the coercive force of the magnetic material included in the paper sheet 100 is determined based on the outputs of the magnetic sensors 10a to 10f at the timing of passage of the paper sheet 100, and if the determined coercive force matches that of the magnetic material used on an authentic paper sheet the paper sheet 100, then it can be determined that the paper sheet 100 is an authentic paper sheet.

In the example shown in FIG. 2A, the two magnets 30, 40, the first magnetic sensor 10, and the second magnetic sensor 20 form an integrated unit accommodated in one housing. However, the configuration of the magnetic property detection apparatus 1 is not limited to an integrated type unit.

Figure 5A:
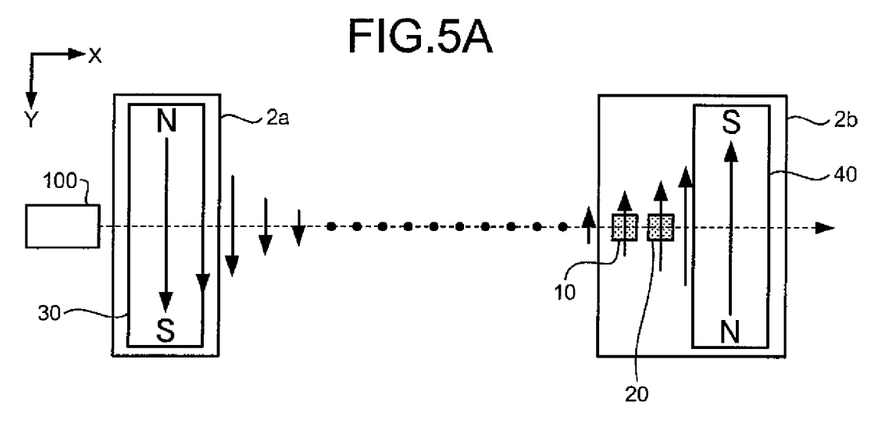
FIGS. 5A and 5B are views that illustrate an example of another configuration of the magnetic property detection apparatus.
Figure 5B:
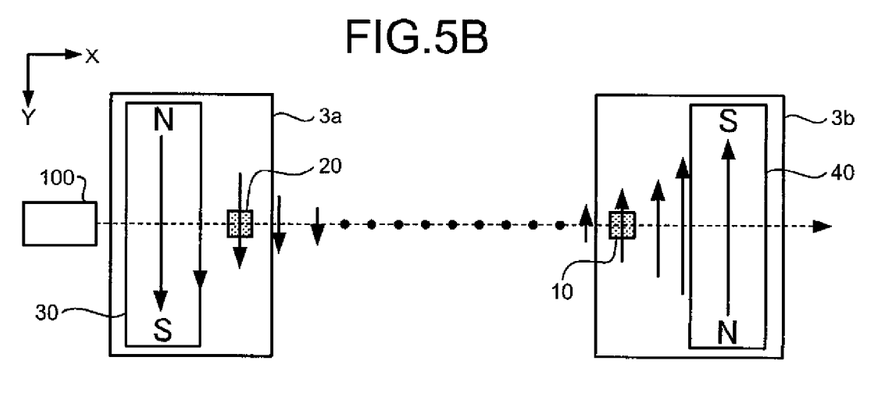

FIG. 5A and FIG. 5B are views that illustrate examples of other configurations of the magnetic property detection apparatus 1. As shown in FIG. 5A, the magnetic property detection apparatus 1 can include a separate unit configuration including a unit 2a including the magnet 30 and a unit 2b including the magnet 40, the first magnetic sensor 10, and the second magnetic sensor 20. As explained above with reference to FIG. 1A to FIG. 1C and FIG. 2A to FIG. 2C, the location of arrangement of the second magnetic sensor 20 can be a position other than the location of arrangement of the first magnetic sensor 10. Accordingly, as shown in FIG. 5B, it is also possible to employ a configuration in which one unit 3a includes the magnet 30 and the second magnetic sensor 20 while the other unit 3b includes the magnet 40 and the first magnetic sensor 10. In the configurations shown in FIG. 5A and FIG. 5B, as is indicated by solid line arrows, the magnetic field intensity decreases as the paper sheet 100 is transported in the transport direction from the location of the magnet 30 arranged in the units 2a, 3a on the upstream side of the first magnetic sensor 10 in the transport direction and reaches 0 (zero) between the units (i.e., between the unit 2a and the unit 2b or between the unit 3a and the unit 3b). After a series of regions of zero magnetic field in which the magnetic field intensity is 0 (zero), a magnetic field with a reverse direction is generated, and the intensity of this magnetic field gradually increases as the paper sheet 100 comes close to the unit 2b, 3b arranged on the downstream side in the transport direction.

Because the second magnetic sensor 20 is arranged above the magnet 40 in the magnetic property detection apparatus 1 shown in FIG. 2A, the location of the magnet 40 on the downstream side in the transport direction is lower than the location of arrangement of the magnet 30 on the upstream side in the transport direction. However, the location of arrangement of the magnets 30 and 40 are not limited to this. The types, the magnetic forces, the shapes, and the like of the magnets are not particularly limited, either.

Figure 6A:
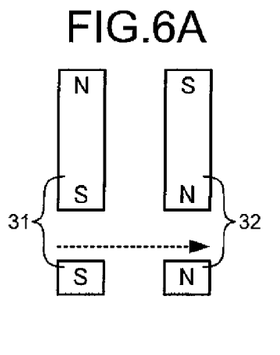
Figure 6B:
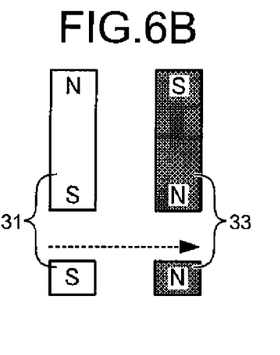
Figure 6C:
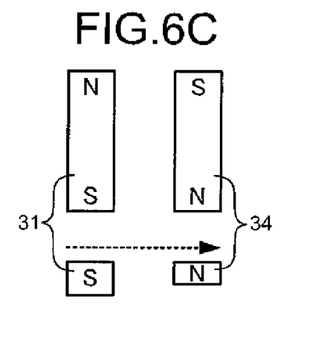

FIG. 6A to FIG. 6C are views that illustrate examples in which the locations of arrangement and the magnetic forces of the two magnets 30 and 40 used in the magnetic property detection apparatus 1 are different from those explained above. The upper portions of FIG. 6A to FIG. 6C illustrate the magnets viewed from above (from the positive side on the Z-axis), and the lower portion illustrate the magnets viewed from the front (from the positive side of the Y-axis). Referring to the lower portion of FIG. 6A, the locations of arrangement of two magnets 31 and 32 in the height direction (Z-axis direction) can be the same as each other. In this case, the second magnetic sensor 20 can be arranged to the side of the magnets 31, 32. The magnetic forces, the types, the shapes, and the like of the two magnets can be differentiated between them. Specifically, different materials can be used for the two magnets 31 and 32 and one magnet 33 can have a magnetic force lower than the magnetic force of the other magnet 31 as shown in FIG. 6B. In yet another alternative configuration, the magnets can have shapes different from each other when viewed from the front as shown in FIG. 6C.

Figure 7A:
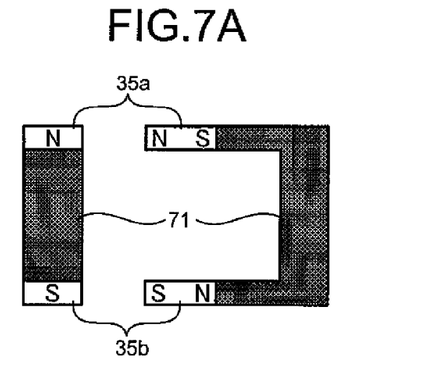
FIGS. 7A and 7B are views that illustrate examples in which the shapes of the magnets used in the magnetic property detection apparatus are different.
Figure 7B:
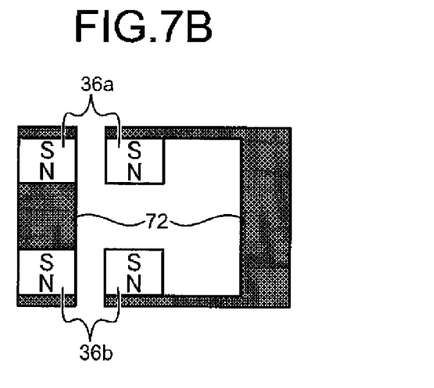

FIG. 7A and FIG. 7B are views that illustrate examples in which the magnets used in the magnetic property detection apparatus 1 have shapes different from those explained above. In FIG. 7A and FIG. 7B, the left portion thereof shows the magnets when viewed from above (from the positive side on the Z-axis) while the right portion thereof shows the magnets when viewed from the side (from the positive side on the X-axis). In the magnetic property detection apparatus 1 shown in FIG. 2A, the magnets 30 and 40 have a rectangular solid shape. However, the magnets 30 and the magnet 40 can have a shape in which two magnets 35a and 35b are attached on both end faces of a yoke 71 having a U-shaped side surface, as shown in FIG. 7A. In an alternative configuration, two magnets 36a and 36b may be attached to a yoke 72 having a U-shaped side surface on its inner sides of both ends thereof, as shown in FIG. 7B.

Figure 8A:
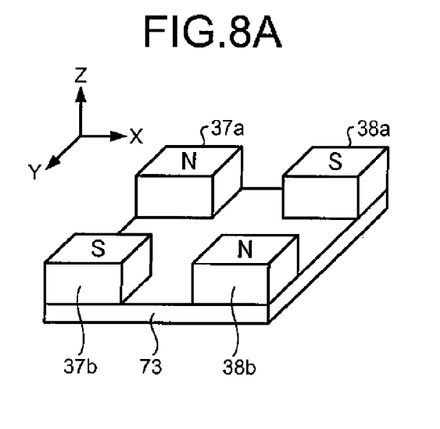
FIGS. 8A and 8B are views that illustrate examples in which the configurations of the magnets used in the magnetic property detection apparatus are different.
Figure 8B:
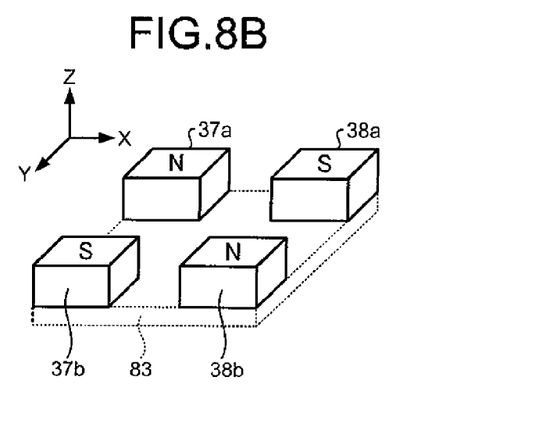

FIG. 8A and FIG. 8B are views that illustrate examples in which the configurations of the magnets used in the magnetic property detection apparatus 1 are different from that explained above. In FIG. 8A and FIG. 8B, four magnets are used as two pairs of magnets. The direction of the magnetic field generated by magnets 37a and 37b and the direction of the magnetic field generated by magnets 38a and 38b are opposite to each other, and thereby the magnetic field similar to that shown in FIGS. 1 and 2 can be generated. In this configuration, the magnets can be attached onto a yoke 73 with a flat shape as shown in FIG. 8A or the magnets can be fixed onto a nonmagnetic material 83 to be used, as shown in FIG. 8B.

The types, the magnetic forces, the shapes, the numbers, the locations of arrangement, the presence or absence of a yoke, and the like are not particularly limited if the magnetic field is generated in a direction perpendicular to the direction of transport of the paper sheet 100 and parallel to the transport surface of the paper sheet 100 and if the intensity of this magnetic field gradually decreases and if the magnetic field intensity increases with the magnetic field being directed in the reverse direction after the magnetic field intensity has reached 0 (zero), and accordingly, the magnet unit can be formed by using a variety of magnets.

Figure 9A:
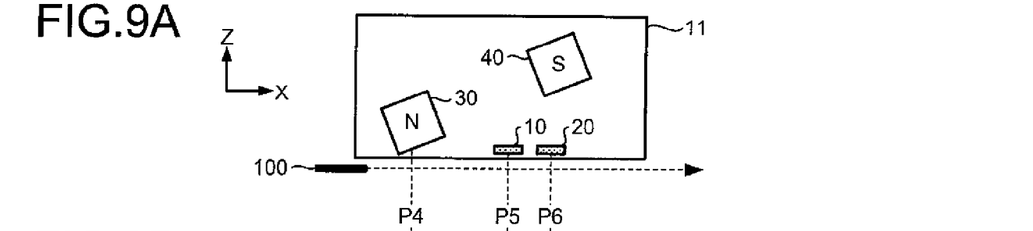
FIGS. 9A, 9B, 9C, 9D, 9E and 9F are views that illustrate an example of another configuration of the magnetic property detection apparatus.
Figure 9B:
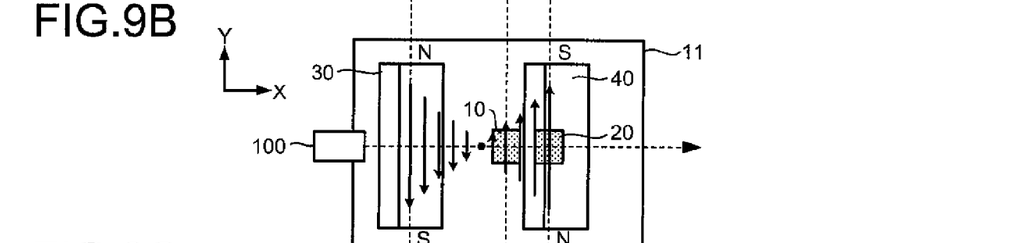
Figure 9C:
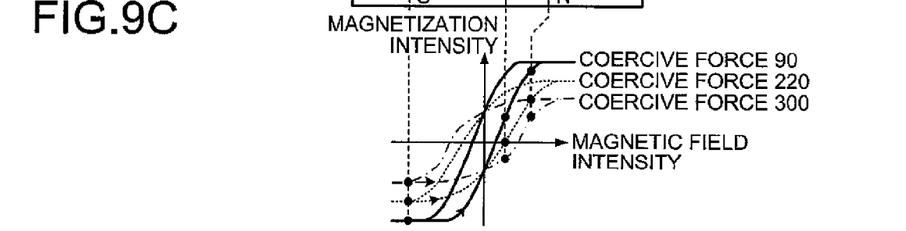
Figure 9D:
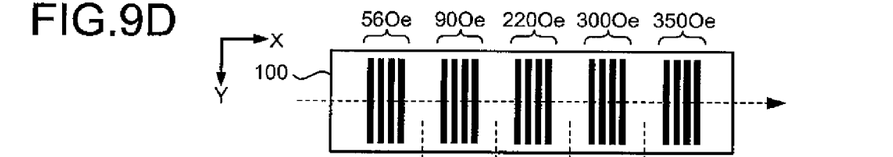
Figure 9E:
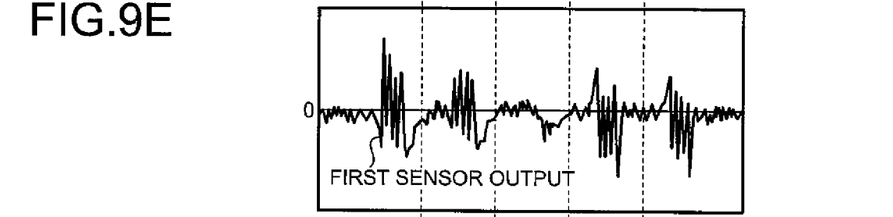
Figure 9F:
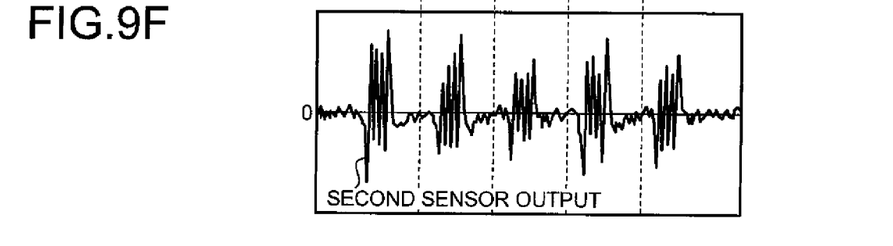

FIG. 9A to FIG. 9F are views that illustrate examples of yet another configuration of the magnetic property detection apparatus. FIG. 9A is a view that illustrates a magnetic property detection apparatus 11 when viewed from the front (from the positive side on the Y-axis), and FIG. 9B is a view that illustrates the magnetic property detection apparatus 11 when viewed from below (from the negative side on the Z-axis). FIG. 9C shows saturation magnetization curves for the magnetic inks to be detected. FIG. 9D shows a paper sheet 100 including a plurality of types of magnetic inks as an example of the object of the detection. FIG. 9E and FIG. 9F show detection signals acquired by the magnetic property detection apparatus 11 when the magnetic material included in the paper sheet 100 is detected.

The magnetic property detection apparatus 11 shown in FIG. 9A, is different from the magnetic property detection apparatus 1 shown in FIG. 2A in a point such that the magnetic property detection apparatus 11 is arranged above the transport path through which the paper sheet 100 is transported, and in the arrangement of the magnets 30 and 40 and the location of arrangement of the first magnetic sensor 10 and the second magnetic sensor.

Specifically, the magnets 30 and 40 are arranged in an inclined state so that they form an angle with the direction of transport of the paper sheet 100 (the X-axis) when viewed from the front (from the positive side on the Y-axis). The two magnets 30 and 40 are arranged at different height locations (i.e., at different locations in the Z-axis direction). More specifically, the magnet 30 located at the magnetization position P4 on the upstream side in the transport direction is located at a position closer to the transport path, while the magnet 40 on the downstream side is located at a position more distant from the transport path than the upstream-side magnet 30 in the height direction.

The first magnetic sensor 10 is arranged at a position P5 at which the magnetization intensity is 0 (zero) when the magnetic ink with the coercive force of 220 Oe having been magnetized into the saturation magnetization state at the position P4 is transported, similarly to the example shown in FIG. 2B. The second magnetic sensor 20 is arranged at a location at a position P6 on the downstream side of the first magnetic sensor 10 in the transport direction in the magnetic field.

Referring to FIG. 9D, assume that a paper sheet the paper sheet 100 on which magnetic patterns formed by four straight lines have been formed by using magnetic inks with the coercive force of 56 Oe, 90 Oe, 220 Oe, 300 Oe, and 350 Oe is transported in the manner shown in FIGS. 9A and 9B. Then, a detection signal shown in FIG. 9E is acquired from the first magnetic sensor 10 while a detection signal shown in FIG. 9F is acquired from the second magnetic sensor 20, for example. In FIG. 9D to FIG. 9F, the magnetic patterns shown in FIG. 9D and the detection signals from the respective sensors obtained in relation to the respective magnetic patterns are aligned and shown so as to be vertically arranged to facilitate understanding.

The magnetic field is generated and the first magnetic sensor 10 and the second magnetic sensor 20 are arranged as shown in FIG. 9A to FIG. 9C, and thereby the detection signals shown in FIG. 9E and FIG. 9F are acquired from the respective sensors. Specifically, a detection signal corresponding to the magnetic ink with the coercive force of 220 Oe acquired from the first magnetic sensor 10 is substantially 0 (zero) as shown in FIG. 9E, while for the magnetic ink with the coercive force of 56 Oe and the magnetic ink with the coercive force of 90 Oe, which are lower than 220 Oe, four peaks are formed, which correspond to four magnetic patterns on the positive side, formed as the value falls from substantially 0 (zero) into the negative side once and then rises to the positive side, as shown in FIG. 9E. For the magnetic ink with the coercive force of 300 Oe and the magnetic ink with the coercive force of 350 Oe, which are higher than 220 Oe, four peaks are formed, which correspond to four magnetic patterns on the negative side, formed as the value rises from substantially 0 (zero) into the positive side once and then falls to the negative side, as shown in FIG. 9E.

On the contrary, for the detection signal acquired by the second magnetic sensor 20, when the magnetic ink with the coercive force of 220 Oe has been detected, four peaks are formed on the positive side, which are formed as the signal falls from substantially 0 (zero) into the negative side once and then rises to the positive side, as shown in FIG. 9F. For the magnetic ink with the coercive force of 56 Oe and the magnetic ink with the coercive force of 90 Oe, detection signals in the same phase as that acquired from the first magnetic sensor 10 are acquired. For the magnetic ink with the coercive force of 300 Oe and the magnetic ink with the coercive force of 350 Oe, detection signals in the phase opposite from that acquired from the first magnetic sensor 10 are acquired.

As explained above, also in the magnetic property detection apparatus 11 shown in FIG. 9A and FIG. 9B, if the output value of the first magnetic sensor 10 is substantially 0 (zero) while magnetism has been detected by the second magnetic sensor 20, it can be determined that the magnetic material is the magnetic ink with the coercive force of 220 Oe. If the output from the first magnetic sensor 10 and the output from the second magnetic sensor 20 are signals in the same phase, then it can be determined that the magnetic material is a magnetic ink with the coercive force lower than 220 Oe, while if the output from the first magnetic sensor 10 and the output from the second magnetic sensor 20 are signals in the phase opposite from each other, then it can be determined that the magnetic material is a magnetic ink with the coercive force higher than 220 Oe.

As explained above, according to the present embodiment, the magnetic property detection apparatus 1 or 11 is arranged either below or above the transport path for transporting the paper sheet 100. Accordingly, the apparatus size can be reduced, and as a result, the production costs can be reduced. If the present invention is used for determination of authenticity of a paper sheet in a paper sheet handling apparatus, the present invention can be easily assembled to the paper sheet handling apparatus, and the magnetic property detection apparatus 1 or 11 can be newly added to the existing paper sheet handling apparatus in the transport path thereof and used therein.

If the magnetic property detection apparatus 1 or 11 is arranged either above or below the transport path, the paper sheet 100 can be stably transported by transport rollers and the like arranged on the other side of the transport path that constitute a part of the transport mechanism. If the paper sheet 100 is pressed onto the transport path by using the transport rollers and the like, the magnetism of the magnetic material included in the paper sheet 100 can be stably detected as no gap is produced between the magnetic property detection apparatus 1 or 11 and the paper sheet 100.

INDUSTRIAL APPLICABILITY

As explained above, the present invention is a technique useful for detecting a magnetic ink used on a valuable medium.

EXPLANATION OF REFERENCE NUMERALS 1, 11 magnetic property detection apparatus
10 first magnetic sensor
10a to 10f magnetic sensor
20 second magnetic sensor
30 to 38 and 40 magnet
70 to 73 yolk
83 nonmagnetic material
100 paper sheet

The invention claimed is:

1. A magnetic property detection apparatus that detects magnetic properties of a magnetic material included in a paper sheet transported through a transport path, comprising:
    a magnet unit that generates a magnetic field that is perpendicular to a direction of transport of the paper sheet in the transport path and parallel to a transport surface of the paper sheet, of which magnetic field intensity decreases as the paper sheet is being transported in the transport direction, and after the magnetic field intensity has reached 0 (zero), the magnetic field intensity increases with the magnetic field being directed in a reverse direction; and
    a plurality of magnetic sensors arranged in the magnetic field generated by the magnet unit at locations at which the magnetic field intensity are mutually different, and that detect the magnetic properties of the paper sheet being transported through the transport path,
    wherein the magnetic properties of the magnetic material included in the paper sheet are detected based on output signals of the plurality of magnetic sensors acquired when the magnetic material is detected.

2. The magnetic property detection apparatus according to claim 1, further comprising an authenticity determining unit that determines, if a magnetic material included in an authentic paper sheet has been detected and if an output value of a specific magnetic sensor of the plurality of magnetic sensors is 0 (zero), that the paper sheet includes a magnetic material having a specific magnetic property on condition that an output value of any magnetic sensor other than the specific magnetic sensor, of the plurality of magnetic sensors, is other than 0 (zero), and determines that the paper sheet of which magnetism has been detected is an authentic paper sheet.

3. The magnetic property detection apparatus according to claim 1, further comprising an authenticity determining unit that determines that if a magnetic material included in an authentic paper sheet has been detected and if no magnetic sensor among the plurality of magnetic sensors exists of which an output value thereof is substantially 0 (zero), the paper sheet to be detected includes a magnetic material having a specific magnetic property when phases of outputs of two specific mutually adjacent magnetic sensors among the plurality of magnetic sensors are opposite to each other, then determines that the paper sheet of which magnetism has been detected is authentic.

4. The magnetic property detection apparatus according to claim 3, wherein the first magnetic sensor is arranged at a position at which the magnetization intensity becomes 0 (zero) after the magnetic material having been magnetized into a saturation magnetization state in the magnetic field is transported in the transport direction based on the magnetization characteristics of the magnetic material having a specific coercive force.

5. The magnetic property detection apparatus according to claim 4, wherein if no magnetism has been detected by the first magnetic sensor and if magnetism has been detected by the second magnetic sensor, it is judged that the magnetic material is the magnetic material having a specific coercive force.

6. The magnetic property detection apparatus according to claim 4, wherein the coercive force of the detected magnetic material is judged based on phases of a magnetism detection signal output from the first magnetic sensor and a magnetism detection signal output from the second magnetic sensor.

7. The magnetic property detection apparatus according to claim 1, further comprising:
 a first magnetic sensor that detects magnetic properties of the paper sheet transported through the transport path at a position set based on magnetization characteristics of the magnetic material having a specific coercive force in the magnetic field generated by the magnet unit; and
 a second magnetic sensor that detects magnetic properties of the paper sheet transported through the transport path at a position different from the position of the first magnetic sensor.

8. The magnetic property detection apparatus according to claim 7, wherein the first magnetic sensor is selected from among the plurality of magnetic sensors arranged at positions at which the magnetic field intensity levels are mutually different based on outputs of the respective magnetic sensors obtained when the magnetic material to be detected is transported through the transport path.

9. The magnetic property detection apparatus according to claim 8, wherein when the magnetic material is transported, a magnetic sensor that outputs a positive output and a magnetic sensor arranged adjacent to the magnetic sensor and that outputs a negative output are selected among the plurality of magnetic sensors and the two magnetic sensors are used as the first magnetic sensor.

10. The magnetic property detection apparatus according to claim 1, wherein the magnet unit at least includes:
 a first magnet that generates a magnetic field in a direction perpendicular to the direction of transport of the paper sheet and parallel to the transport surface of the paper sheet; and
 a second magnet that generates a magnetic field directed reversely from the direction of the magnetic field generated by the first magnet on a downstream side of the first magnet in the transport direction.

11. The magnetic property detection apparatus according to claim 1, wherein the magnetic field generated by the magnet unit has magnetic field intensity for magnetizing the magnetic material to be detected into a saturation magnetization state at a position upstream of the first magnetic sensor in the transport direction.

12. The magnetic property detection apparatus according to claim 1, wherein in the magnetic field generated by the magnet unit, the magnetic field intensity gradually decreases to reach 0 (zero), then a series of regions of zero magnetic field continues to be present, and then the magnetic field intensity increases with the magnetic field being directed in a reverse direction.

13. The magnetic property detection apparatus according to claim 1, further comprising an adjustment mechanism for changing the magnetic field intensity at a position of arrangement of the first sensor.

14. The magnetic property detection apparatus according to claim 1, wherein the first magnetic sensor and the second magnetic sensor are sensors that detect variations of intensity of magnetic flux occurring due to passage of a magnetized magnetic material through a magnetic field.

* * * * *